United States Patent [19]

Marik et al.

[11] Patent Number: 5,417,694
[45] Date of Patent: May 23, 1995

[54] DISTAL FEMORAL CUTTING GUIDE APPARATUS WITH ANTERIOR OR POSTERIOR REFERENCING FOR USE IN KNEE JOINT REPLACEMENT SURGERY

[75] Inventors: Gregory C. Marik, Collierville; Jennifer J. Lackey; M. Scott Elliott, both of Memphis, all of Tenn.

[73] Assignee: Smith & Nephew Richards Inc., Memphis, Tenn.

[21] Appl. No.: 149,053

[22] Filed: Nov. 8, 1993

[51] Int. Cl.⁶ .............................................. A61B 17/00
[52] U.S. Cl. ............................................ 606/88; 606/96
[58] Field of Search ....................... 606/79, 80, 81, 82, 606/84, 86, 87, 88, 96, 102, 62–65

[56] References Cited

U.S. PATENT DOCUMENTS

| | | | |
|---|---|---|---|
| 4,487,203 | 12/1984 | Androphy | 606/88 |
| 4,653,488 | 3/1987 | Kenna et al. | 606/88 |
| 4,721,104 | 1/1988 | Kaufman et al. | 606/88 |
| 4,935,023 | 6/1990 | Whiteside et al. | 606/80 X |
| 5,053,037 | 10/1991 | Lackey | 606/80 X |
| 5,234,433 | 8/1993 | Bert et al. | 606/88 |
| 5,250,050 | 10/1993 | Poggie et al. | 606/88 X |

Primary Examiner—Peter A. Aschenbrenner
Attorney, Agent, or Firm—Pravel, Hewitt, Kimball & Krieger

[57] ABSTRACT

A distal femoral cutting instrument includes an intramedullary rod for referencing the patient's intramedullary canal. A valgus block with a flat reference surface mounts to the intramedullary rod at a bore of the valgus block. The bore of the block has a slant with respect to the flat reference surface on the valgus block. The reference surface defines a line that is normal to the mechanical axis of the patient while the bore of the valgus block tracks the patient's biomechanical axis. A distal femoral cutting block removably attaches to the valgus block and provides a flat cutting guide surface for shaping the patient's distal femur. The valgus block, intramedullary rod, and a stylus (for connecting the valgus block and cutting together) are removed as a unit before shaping of the distal femur. An indexing system includes a gauge having a series of openings corresponding to "anterior" referencing and to "posterior" referencing. During anterior referencing, the gauge allows the surgeon to select the next smaller size prosthesis if the size falls in between available sizes. In posterior referencing, the gauge allows the surgeon to select the next larger size prosthesis if the gauge measures a size that falls in between available sizes.

14 Claims, 7 Drawing Sheets

DISTAL FEMORAL CUTTING GUIDE APPARATUS WITH ANTERIOR OR POSTERIOR REFERENCING FOR USE IN KNEE JOINT REPLACEMENT SURGERY

BACKGROUND OF THE INVENTION

1. Field of the Invention

The present invention relates to surgical orthopedic cutting instruments, and more particularly relates to an improved cutting block apparatus for shaping the distal femur of a patient prior to the placement of a knee joint prosthesis. Even more particularly, the present invention relates to a distal femoral cutting block apparatus that allows a surgeon to select a knee prosthesis using an anterior or a posterior referencing technique when the anterior/posterior dimension falls in between available inventory sizes (typically one or more millimeters apart in size).

2. General Background

In knee joint replacement surgery, the surgeon often replaces the distal femoral surface of the patient's knee with a curved metallic prosthesis. The prosthesis has a generally smooth continuous outer curvature that faces a corresponding component that is attached to the patient's tibia. The posterior surface of the femoral component is typically provided with a number of intersecting flat surfaces. A common femoral component of a knee prosthesis provides five intersecting flat surfaces. One of the surfaces is adapted to engage the anterior cortical surface of the femur. Another of the flat surfaces is adapted to face the posterior surface of the femur. Yet another surface is adapted to engage the distal end of the patient's femur. Additionally, a pair of chamfer surfaces form diagonally extending surfaces which form an interface between the distal surface and the respective anterior and posterior surfaces.

A surgeon forms five (5) separate cuts on the patient's distal femur in order to prepare the distal femur to receive the femoral prosthesis. One of the problems facing the surgeon is the proper orientation of the cuts so that the prosthesis will fit the femur with the correct orientation. One method of orienting a cutting guide is to reference that cutting guide to a rod that is placed in the patient's intramedullary canal.

A number of patents have issued which disclose medical cutting instruments for use by orthopedic surgeons. Some of these cutting instruments relate to shaping of the distal femur or adjacent bone structure.

U.S. Pat. No. 4,474,177 is an example of a cutting block instrument that references a cutting guide to an intramedullary rod that is positioned in the patient's intramedullary canal of the femur.

The Whiteside U.S. Pat. No. 4,467,801, entitled "Method And Apparatus For Shaping A Proximal Tibial Surface", provides a method and apparatus for preparing the proximal surface of a tibia to receive a proximal tibial prosthesis employing a reamer/alignment guide which is used to internally locate the central long axis of the tibia and a plateau planar which cooperatively engages with a guide handle attached to the reamer/alignment guide to accomplish the shaping of the proximal tibial surface. The reamer/alignment guide has a rod portion extending into the interior of the tibial shaft whose central long axis corresponds with the central long axis of the tibia. The guide handle is concentric with that rod portion such that the plateau planar assumes the proper alignment with respect to the central long axis of the tibia such that the proximal tibial surface is shaped relative to that axis in a simple and accurate manner.

European Patent Application No. 0 122 669 discloses a guide for femoral neck osteotomy that comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongate planar surface disposed at an angle of 45° to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongate planar surface of the guide bar whereby an instrument in engagement with that surface traverses the femoral neck at an angle of 45° to the long shaft axis of the femur.

Another Whiteside U.S. Pat. No. 4,474,177 provides a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. The intramedullary alignment guide has a rod portion extending into the femoral intramedullary canal whose central long axis corresponds with the central long axis of the femur. The guide handle is attached to that rod portion at a preselected angle such that the shaping instruments fixed thereto assume the proper alignment with respect to the central long axis of the femur such that the distal femoral surface is shaped relative to that axis in a simple and accurate manner.

An improved triplanar knee resection system, disclosed in U.S. Pat. No. 4,487,203, provides a system for preparing a knee joint for a prosthesis. The apparatus of the triplanar knee system includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by an orthopedic surgeon in properly preparing a knee joint for implantation of a prosthesis.

U.S. Pat. No. 4,567,885 also provides an improved triplanar knee resection system for preparing a knee joint for a prosthesis. The apparatus of the triplanar knee system includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by ann orthopedic surgeon in properly preparing a knee joint for implantation of a prosthesis.

The Petersen U.S. Pat. No. 4,567,886 discloses a spacer guide for utilization in total knee surgery for establishing size of prosthesis and position of cuts for total knee replacement surgery includes a generally L-shaped base member for attachment to the anterior femoral cortex of a prepared femur with a generally L-shaped adjustable support member adjustably secured to the base support member and a vertically positionable indicator slide having a squaring jig for cooperative engagement and alignment with the cutting head of a tibia alignment and resection guide for squaring the tibia and femur and including indicator means for indicating the position of a tibia plateau cut and indicating the size and positioning for a distal femoral cut for indicating the sizing of the both the tibial and femoral prostheses.

The Kenna et al. U.S. Pat. No. 4,464,729 discloses a prosthetic knee implanted after cutting the femur and tibia with the aid of instruments which include axial alignment guides and a series of cutting jigs.

A method and apparatus for resecting a distal femoral surface is disclosed in U.S. Pat. No. 4,703,751 in which an intramedullary rod is inserted through the distal surface of the femur and along the femoral shaft access, leaving a protruding end; a jig is attached to the protruding end, the gig having a shaft for receiving the rod end and a support plate attached to an end of the shaft and extending parallel to the rod; attaching a reference bar to the shaft, the bar having a pair of opposing flanges and a central opening which receives the shaft therethrough, and adjusting the bar on the shaft such that the flanges contact condylar apices of the femur; fixing the jig relative to the femur; attaching a cutting plate to the jig, the cutting plate having blade guides thereon, pivoting the cutting plate relative to the jig such that the blade guides made a predetermined angle with the rod, and securing the cutting plate to the jig; and inserting a saw blade through the blade guides to make a resection of the distal femoral surface. In the preferred embodiment, the shaft includes a plurality of bores along its length, each sized to receive the rod therethrough so that the distance between the rod and the support plate may be adjusted to accept different sized anterior femur portions. Also in the preferred embodiment, the apparatus includes a plurality of guide bars, each sized to space the blade guides a predetermined distance from the condylar apices.

The Kaufman et al. U.S. Pat. No. 4,721,104 relates to a surgical apparatus for providing an accurately recess in a distal femoral surface for the intercondylar stabilizing housing of a posterior-stabilized knee implant prosthesis which apparatus comprises a template having a bottom surface which is adapted to be placed in an aligning relationship with the flat surface of a distal femur which has been partially shaped to receive the femoral component of a posterior-stabilized knee implant prosthesis and a U-shaped slot passing through the template where the slot is of substantially the same size and shape as the outer periphery of the intercondylar stabilizing housing present on the femoral component to be implanted and a drilling means, preferably in the form of an endmill cutter, having a stop means thereon and the drilling means closely engages the sides of the U-shaped slot in the template so that the drilling means can be passed through the U-shaped slot until the stop means contacts a surface of the guide and is then drawn along the slot to create a precisely shaped and aligned recess in the femur for receipt of the intercondylar stabilizing housing. In a more preferred embodiment, the template is composed of a drilling means guide which fits over a femoral trial prosthesis which is used for trial reductions after the drill guide is used and removed.

The Russell et al. U.S. Pat. No. 4,722,330 relates to distal femoral surface shaping guide for mounting on a intramedullary alignment guide which references the central long axis of the femur in shaping the distal femoral surface and a method for shaping the distal femur using the shaping guide. The alignment guide of the present invention is adjustable relative to the surface of the anterior femoral cortex to insure that the anterior aspect of the distal femoral condyles is resected relative to that surface and, preferably, at the same level as that surface. The alignment guide of the present invention provides a main body which remains attached to the intramedullary alignment guide throughout the entire shaping of the distal femur. It thus requires fewer cutting guides and alignment steps than other shaping guides while allowing greater accuracy in shaping the distal femur relative to the central long axis of the femur.

An improved tibial cutting jig is disclosed in U.S. U.S. Pat. No. 4,736,737, provided for use in obtaining accurate tibial resection in the course of a total knee prosthesis implantation procedure. The tibial cutting jig includes a base for sliding reception onto an intramedullary alignment rod preinstalled generally along the longitudinal axis of the tibia. The base includes laterally extending outriggers carrying removable measurement keys of selected size for spacing the base above the tibial plateau by a selected dimension. An anterior saw guide depends from the base and is thus positioned relative to the tibial plateau in accordance with the sizes of the measurement keys.

The Buechel et al. U.S. Pat. No. 4,738,253 discloses a guide for a cutting device used to make a surgical cut in a first bone in desired spatial relationship with a pre-existing cut in a second bone is disclosed to include a means for contacting the pre-existing cut to establish a reference for the desired spatial relationship and a body member engaging the means for contacting and including a guide surface for establishing the desired spatial relationship and guiding a surgical cutting tool to cut the first bone in a plane which is not normally inclined with respect to the long axis of the first bone.

Another Buechel et al. U.S. Pat. No. 4,738,254 discloses a positioner for positioning a surgical instrument which acts as a guide for a cutting instrument which produces a surgical cut in an anatomical structure; in one embodiment the positioner positions a surgical instrument which acts as a guide for the cutting instrument at a predetermined position with respect to a previously resected surface whereby a further resection is made at a predetermined position with respect to the previously resected surface; and in a further embodiment the positioner acts as a adaptor for a surgical instrument which aids in producing surgical sections thereby allowing the surgical instrument to produce surgical cuts at various predetermined positions relative to a previous surgical cut made at one of several levels.

The Dunn et al. U.S. Pat. No. 4,759,350 provides a system of instruments for shaping the distal femur and proximal tibia surfaces to receive components of a knee prosthesis for knee replacement surgery. The system references the femur intramedullary channel with a femoral alignment guide to prepare the distal femur that, in turn, is a reference for several cutting guides for sequential attachment to the femoral alignment guide and prepared bone surfaces whereby the prepared distal femur is prepared to a flat surface that is perpendicular to the patient's mechanical axis with bone surfaces adjacent thereto sectioned to surfaces that are at right angles to that distal femur surface with chamfers therebetween to receive the femur component of a knee prosthesis. A tibial cutting guide is provided for preparing the proximal tibia that consists of a sleeve, with a tube telescoped therein, the ends thereof including pin arrangements for connecting them into the tibia, between the ankle and near the proximal tibia, an open tube end of the tibial cutting guide to receive a rod telescoped therein that mounts a cutting guide platform and includes a screw arrangement for releasably maintaining the road and tube together. The cutting guide platform includes a body with a saw guide slot formed therethrough to receive a saw blade to cut across the proximal tibia to form a surface for accommodating a tibial component of the knee prosthesis, the cutting guide platform body further including an arrangement for securing it to the tibia, slightly below the proximal tibia, and a tibial resection guide for setting a depth of cut across the proximal tibia.

U.S. Pat. No. 4,773,407 issued to Petersen discloses a method and instruments for resection of the distal femur. The instruments include a distal femoral resector and a femoral alignment guide/rod. The distal femoral resector is designed to be attached to the distal femur on a plane filed on the anterior femoral cortex. The distal femoral resector includes a feeler gauge laterally adjustable to adapt to the intercondylar notch of the particular patient and further includes a rotating rod having openings therethrough for fastening pins, which rotating rod is designed to facilitate the placement of the resector on the anterior femoral cortex in a flush manner. The femoral alignment guide/rod includes a plate insertable within a slot in the resector designed for the insertion of the cutting tool and further includes a pivotable rod which may be utilized to align the resector with the mechanical axis of the leg. The rod may then be pivoted to a position facilitating the insertion of a fastening pin through the resector. The method of operation using these instruments is also disclosed.

U.S. Pat. No. 4,892,093 issued to Zarnowski et al. discloses a cutting guide for guiding a saw blade during the preparation of a femur for the implant of the femoral component of a knee prothesis includes guide surfaces for enabling the cutting of all four of the anterior femoral cut, the posterior femoral cut, the anterior chamfer and the posterior chamfer, fully and completely, with certitude and accuracy, while the cutting guide remains located and secured to the femur in a single position on a transverse surface located along the distal femur.

The Dale et al. U.S. Pat. No. 4,893,619 discloses a device for guiding an osteotomy to be performed on the proximal end of a humerus that has a proximal saw guide alignable on a selected surface of the proximal end of the humerus for defining a saw line thereon; a radial arm connecting the saw guide to a distal mechanism for stably aligning the saw guide, the distal alignment mechanism has a pair of opposing lateral and medial epicondyle arms pivotally engagable with the lateral and medial sides of the distal end of the humerus, the epicondyle arms being pivotally mounted in a distal cross arm, the distal end of the radial arm being slidably mounted in the cross arm for distal to proximal slidable movement therein; the proximal end of the radial arm being rotatably connected to the saw guide through a proximal guide bar; the radial arm being supported above the humerus by the proximal guide bar and the epicondyle arms.

U.S. Pat. No. 4,907,578 relates to an improved method and instruments for a resection of the distal femur. The parent application discloses a femoral alignment guide/rod including a plate insertable within a guide slot in the resector which is also used for the guided insertion of a cutting tool. The present invention improves upon this structure by providing an auxiliary attachment member on the resector allowing attachment of a new femoral alignment guide/rod on the resector housing proximal to the cutting tool guide slot, which new guide/rod allows easier access to various resector components. In a further aspect, structure is provided allowing the use of the resector with an intramedullary rod to increase accuracy. In this aspect, a gauge is incorporated in the resector which allows compensation for the angle between the mechanical axis of the leg and the longitudinal extent of the internal cavity of the femur while also allowing compensation or correction for specific anatomical conditions such as, for example, valgus correction.

The Whiteside et al. U.S. Pat. No. 4,935,023 relates to a distal femoral surface shaping guide for mounting on an intramedullary alignment which references the central long axis of the femur in shaping the distal femoral surface and a method for shaping the distal femur using that shaping guide with particular applicability for shaping one condyle for attachment of a unicondylar prosthesis. The alignment guide of the present invention is adjustable relative to the surface of the condyle to insure that the distal femoral condyle is resected relative to that surface. The alignment guide of the present invention utilized visual sighting studs and provides a main body which remains attached to the intramedullary alignment guide throughout the entire shaping of the distal femur.

The Bowman et al. U.S. Pat. No. 4,952,213 discloses an apparatus for placing a bone cutting saw cutting guide adjacent a proximal surface of a human tibia bone having an elongated rod inserted into the tibia for clampingly supporting a rotating bar on the central longitudinal axis of the tibia bone. The bar being extended from the rod and connected to a pivot device which in turn is connected to a support arm that holds a saw cutting guide against a proximal portion of the tibia bone. The rotation angle of the rod determining the medial-lateral inclination of the saw cutting guide and the pivot device determining the anterior-posterior inclination of the saw cutting guide. The support arm is adjustable in length to determine the height of the saw cutting guide.

The Dunn et al. U.S. Pat. No. 4,959,066 provides an osteotomy guide assembly for femoral neck osteotomy and includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with a saddle locator assembly. The saw guide is attached to the support bar by a single locking means which provides for positional adjustment of the saw guide relative tot he support bar in two directions, including adjustment in the anterior-posterior direction along the transverse support bar and axially along the femur via a post which extends from the saw guide.

The Whiteside et al. U.S. Pat. No. 5,002,545 provides a shaping guide to permit accurate shaping of the tibial plateau while saving the anterior cruciate ligament. An alignment rod is located anterior to the anterior cruciate ligament and along the anterior cortex of the intramedullary canal of the tibia provides points of reference for all shaping operations. The shaping guide of the present invention is adjustable with respect to the handle portion of the rod so that the amount of resection of the tibial plateau can be controlled readily by the surgeon by raising or lowering of the cutting guide surfaces for resection of the tibia.

The Mikhail et al. U.S. Pat. No. 5,108,405 discloses a system for performing hip prosthesis revision surgery includes a trial femoral component having a passageway which, upon insertion in the cavity left after removal of the original prosthesis, provides guide means for drilling a channel to receive a guide wire which, upon removal of the trail femoral component, serves as guide means for progressively larger reamers.

SUMMARY OF THE INVENTION

The present invention provides an improved method and apparatus for combined anterior and posterior referencing in the shaping of a patient's distal femur using a cutting apparatus.

In the method of the present invention, a valgus alignment block is first placed onto the distal femur using an intramedullary rod that is partially embedded in the patient's intramedullary canal. The block should be placed with the correct side toward the anterior aspect of the femur, i.e., left toward the anterior aspect of the left femur and right toward the anterior aspect of the right femur.

A distal femoral cutting block and stylus are added to the anterior aspect of the valgus alignment block. The distal femoral cutting block is then pinned into place on the anterior aspect of the distal femur. After pinning the distal femoral cutting block into position, the intramedullary rod is removed. The surgeon also removes the valgus alignment block and stylus assembly by sliding the whole assembly distally. Using the distal femoral cutting block that remains on the anterior aspect of the distal femur, the surgeon makes the distal femoral cut. The distal femoral cutting block provides a transversely extending slot that provides a flat surface for reference when shaping the distal femur. A flat cutting blade is preferably used, registering upon the flat surface of the slot portion of the distal femoral cutting block.

After the distal femoral cut has been made, a gauge assembly is placed on the distal femoral cut. The gauge assembly includes a paddle body having a pair of feet or paddles that rest on their respective posterior condyles. An anterior cutting block slidably engages the paddle body so that the two parts telescope between larger and smaller dimensions. The paddle is then pinned onto place so that the feet of the paddle always engage the respective posterior condyles. After the paddle is pinned into position, the anterior cutting guide slides into the slot of the posterior paddle body. The anterior cutting guide slides posteriorly until the anterior referencing feeler gauge finger makes contact with the highest point on the anterior cortex.

For an anterior referencing technique, the surgeon reads the size of the femoral prosthesis that is needed from the assembly of components that are available. If the size however falls between sizes, the block is pinned into place in the hole of the next smallest component on the side labeled "a" for the anterior row of openings.

If a posterior referencing technique is used, the surgeon reads the size of the component needed from the assembly of components. If the size falls between sizes, the surgeon slides the anterior cutting guide anteriorly until the next larger size aligns with the marking on the posterior paddles. Then the surgeon pins the anterior cut guide through the hole of the size selected on the side labeled "p" or posterior.

The surgeon then makes the anterior cut through the anterior cut guide at a slot provided on the guide.

The surgeon then places the anterior/posterior cutting block onto the anterior femoral cut surface and abutting the distal femoral cut surface. The surgeon then pins the block into place.

After the anterior/posterior cutting block is pinned into position, the surgeon cuts the remaining cuts through the anterior/posterior cutting block including the posterior condyles cut, and two chamfer cuts.

The surgeon then places a trial prosthesis on the distal femur and if the fit is good, drills lug holes corresponding in size and shape to the lugs on the rear surface of the femoral prosthesis.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
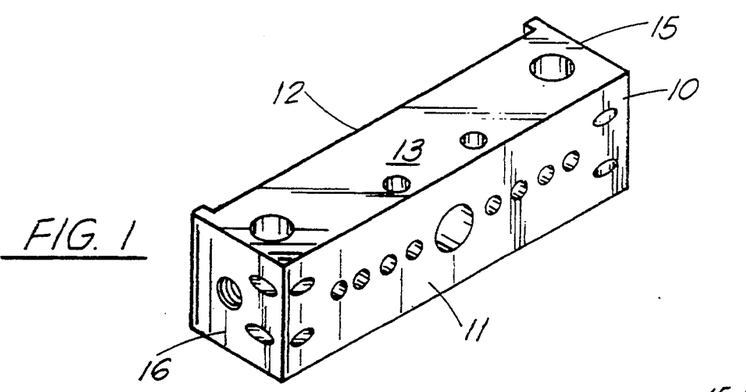
FIG. 1 is a partial perspective view of the preferred embodiment of the apparatus of the present invention illustrating the valgus block portion thereof.
Figures 2, 3, 4, 5, 6:
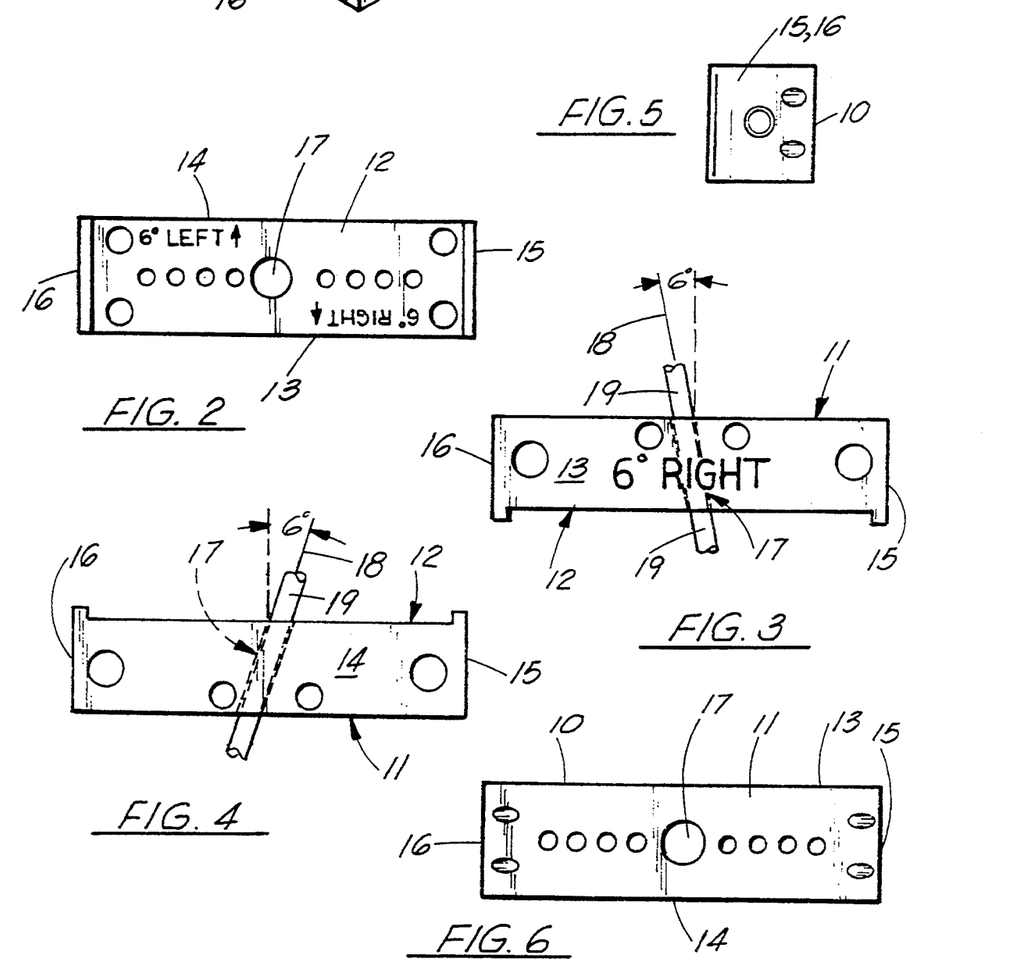
FIG. 2 is a top view of the valgus block portion of the preferred embodiment of the apparatus of the present invention.
FIGS. 3 and 4 are side views of the valgus block portion of the preferred embodiment of the apparatus of the present invention.
FIG. 5 is an end view of the valgus block portion of the preferred embodiment of the apparatus of the present invention.
FIG. 6 is a bottom view of the valgus block portion of the preferred embodiment of the apparatus of the present invention.
Figure 7:
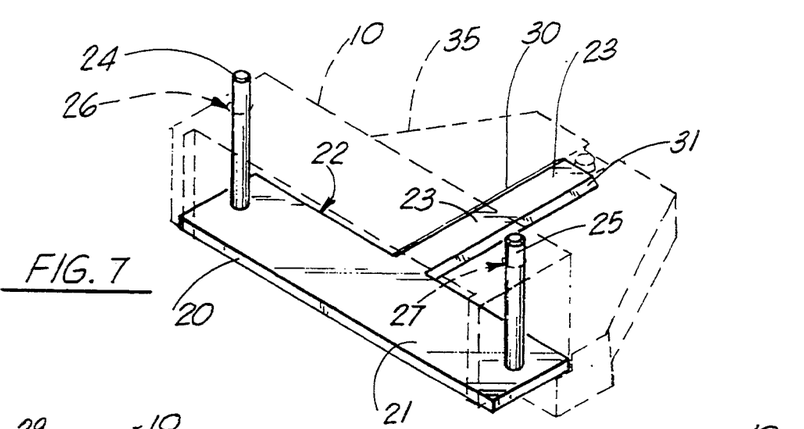
FIG. 7 is a perspective fragmentary view of the preferred embodiment of the apparatus of the present invention illustrating the stylus portion and its connections to the valgus block and distal femoral cutting block (in phantom lines)
Figure 8:
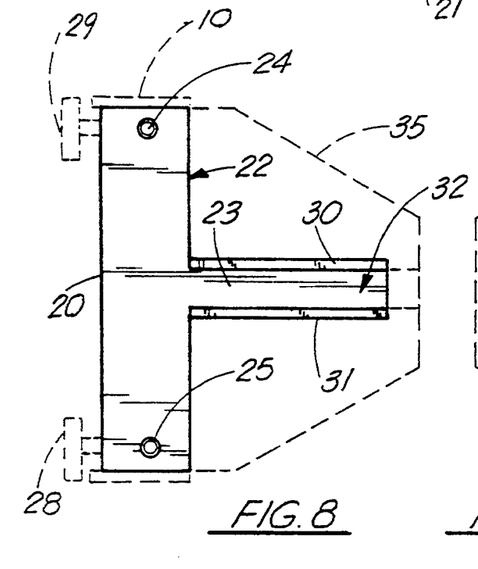
FIGS. 8 and 9 are top and bottom views of the stylus portion of the preferred embodiment of the apparatus of the present invention.
Figure 9:
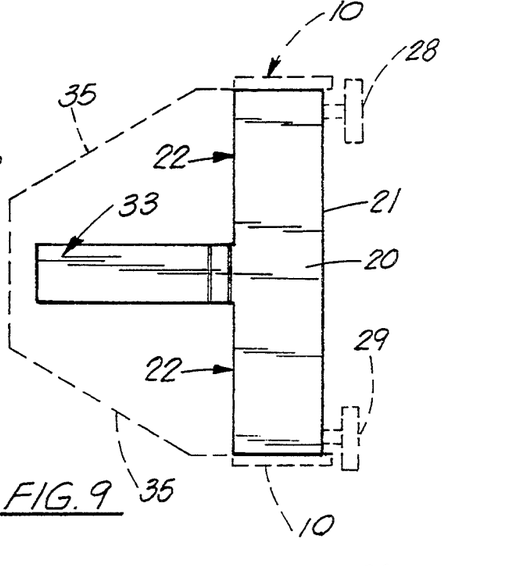
Figure 10:
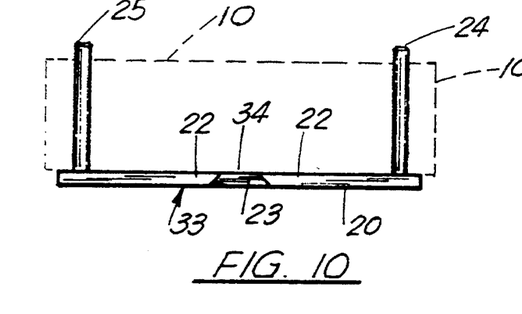
FIGS. 10 and 11 are front and side views of the stylus portion of the preferred embodiment of the apparatus of the present invention.
Figure 11:
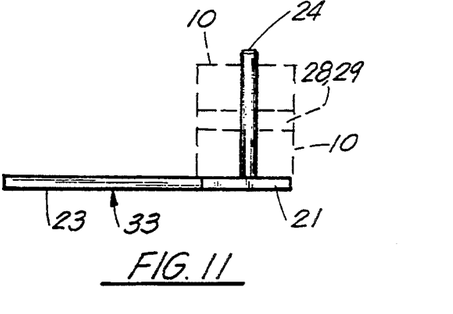

FIGS. 1–5 showing the valgus block 10 portion of the preferred embodiment of the apparatus of the present invention. Valgus block 10 includes a proximal flat surface 11, a distal flat surface 12, and additional flat surfaces 13, 14. The side walls 15, 16 are also flat so that the valgus block can be a generally rectangular prism in shape as shown in the drawings. An angled bore 17 extends between the proximal flat surface 11 and distal flat surface 12. Angled bore 17 is preferably a six degree (6°) angle as shown in FIGS. 3 and 4 with respect to a line that is normal to the proximal and distal surfaces. The angled bore 17 has a bore axis 18 that also defines the central longitudinal axis of intramedullary rod 19 during initial referencing using the valgus block.

In FIGS. 7–11, valgus block 10 is shown as connected to stylus 20. Stylus 20 is a generally T-shaped member that includes a base flange 21 and an arm 23. Base flange 21 provides a flat leading edge 22 that generally aligns with the proximal flat surface 11 of valgus block 10 upon assembly as shown in the drawings.

The base flange 21 of stylus 20 has a pair of posts 24, 25 extending therefrom at opposite end portions of base flange 21. Posts 24, 25 register in openings 26, 27 of valgus block 10 upon assembly. Further, the upper surface 32 of stylus 20 is generally flat and registers in face-to-face relationship with the selected surface 13 or 14 of valgus block 10 depending upon whether the surgeon is operating on the left or right leg of the patient. Block 10 should be placed with the correct side toward the anterior aspect of the femur, i.e., left toward the anterior aspect for the left femur, and right toward the anterior aspect for a right femur.

Upon assembly of valgus block 10 to stylus 20 at posts 24, 25, the stylus 20 and valgus block 10 can be locked together using locking nuts 28, 29. Each locking nut 28, 29 threadably engages valgus block 10 adjacent openings 26, 27. Each locking nut 28, 29 is threadably engages an internally threaded bore so that upon tightening, the locking nuts 28, 29, engage the posts 24, 25 to tighten the block 10 against the posts 24, 25 and thus attach the stylus 20 to the block 10.

Stylus 20 forms a connection with an additional, third portion of the instrumentation. The third portion of the instrumentation is the distal femoral cutting block 35. Distal femoral cutting block 35 has a trapezoidal shape as shown in the drawings. The distal femoral cutting block 35 attaches to stylus 20 with a dove-tail type connection. Stylus 20 arm 23 has beveled surfaces, 30, 31 that provide a dove-tail shaped section 34 (see FIG. 10) that fits in a correspondingly shaped dove-tail slot 36 formed on the upper surface of distal femoral cutting block 35.

Figures 12, 13, 14, 15:
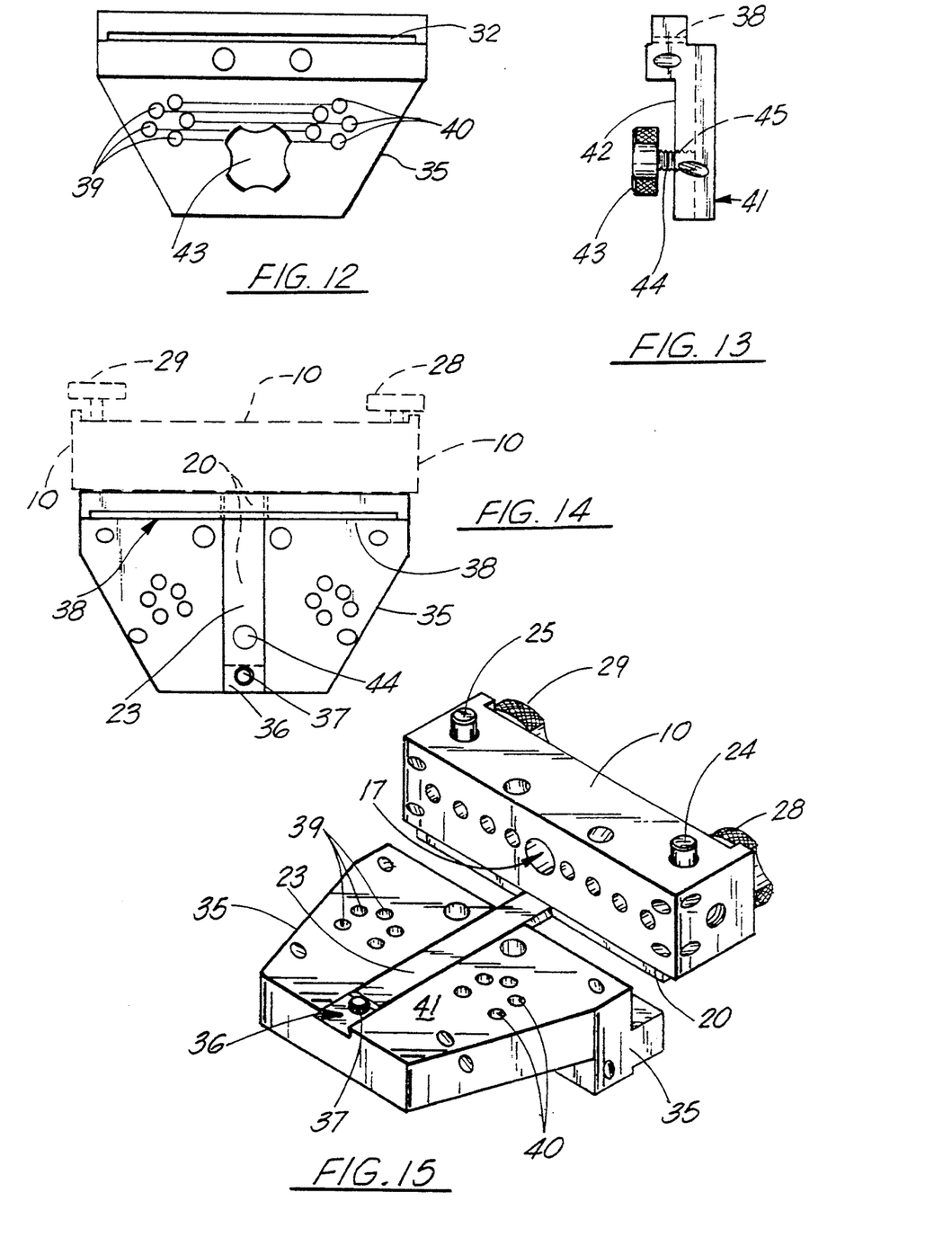
FIG. 12 is a rear view of the distal femoral cutting block portion of the preferred embodiment of the apparatus of the present invention.
FIG. 13 is a side view of the distal femoral cutting block.
FIG. 14 is a frontal view of the distal femoral cutting block portion of the preferred embodiment of the apparatus of the present invention.
FIG. 15 is a fragmentary perspective view of the preferred embodiment of the apparatus of the present invention illustrating the valgus block, distal femoral cutting block, and stylus connected together in operative position.

FIGS. 12–15 further illustrate distal femoral cutting block 35. In FIG. 15, there can be seen the assembly of valgus block 10, stylus 20, and distal femoral cutting block 35. Dove-tail slot 36 carries post 37 which functions as a stop for defining the extent of movement of arm 23 into slot 36.

In FIG. 15, the arm 23 of stylus 20 has extended fully into dove-tailed slot 36 so that the extreme end portion of arm 23 as engaged post 37. Distal femoral cutting block 35 provides a transverse slot 38 that is used to guide a cutting instrument, such as a flat surgical saw 48, during a cutting of the distal femoral femur F (see FIGS. 14 and 18–19). Locking screw 43 has threaded shaft 44 engaging opening 44 to clamp arm 23 in position at slot 36.

Figure 16:
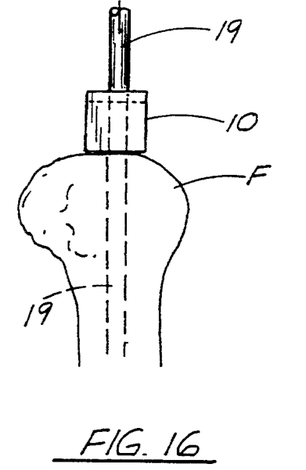
FIGS. 16 and 17 are side and front views of a patient's distal femur illustrating the intramedullary rod and valgus block portions of the preferred embodiment of the apparatus of the present invention thereon and illustrating the first step of the method of the present invention.
Figure 17:
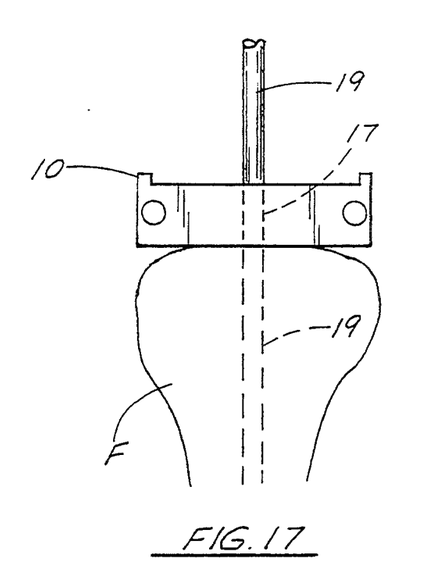

As part of the method of the present invention, the surgeon preliminarily places one end portion of an intramedullary rod 29 into the patient's distal femur F so that rod 19 occupies the patient's intramedullary canal, as shown in FIGS. 15 and 16. Valgus block 10 is mounted upon intramedullary rod 19 so that the intramedullary rod 19 occupies angled bore 17 of block 10. The surgeon simply selects the block 10 having the desired angle (for example, 6°), that will compensate for the patient's valgus angle to produce a desired orientation of cut on the patient's distal femur. For example, if the surgeon selects a 6° block, the cut made on the anterior distal femur using cutting block 35 and transverse slot 28 will be offset by 6° with reference to the central longitudinal axis of the patient's intramedullary canal as defined by intramedullary rod 19. This distal cut is normal to the patient's mechanical axis.

As part of the method, the surgeon then adds the stylus 20 and the distal femoral cutting block 35 to the valgus block 10 as shown in FIGS. 7–11 and 18. Once the distal femoral cutting block 35 and stylus 20 have been assembled to valgus block 10, the distal femoral cutting block is rigidly affixed to the anterior aspect of the patient's distal femur using bone pins inserted through openings 39 and 40.

Figure 18:
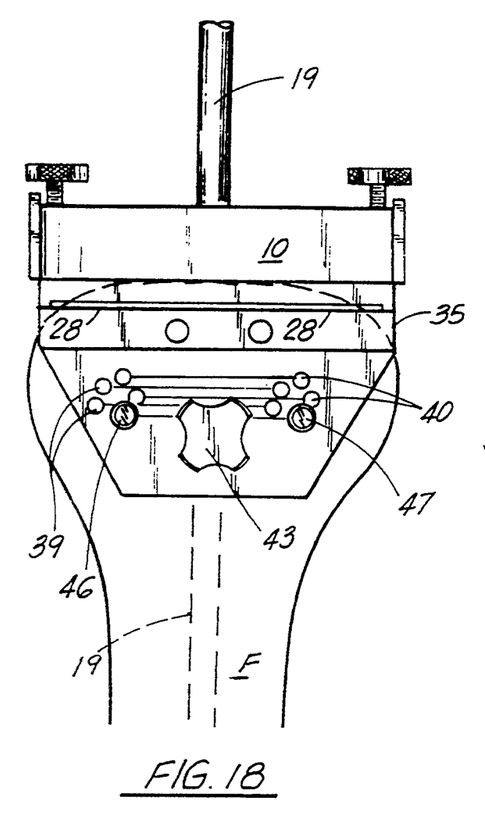
FIG. 18 is an anterior view of the preferred embodiment of the apparatus of the present invention illustrating the valgus block, intramedullary rod, stylus, and distal femoral cutting block portions thereof in place on the patient's distal femur and illustrating a part of the method of the present invention.
Figure 19:
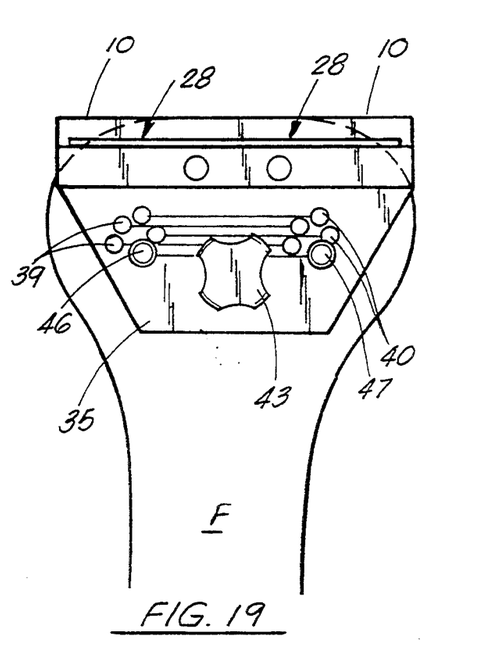
FIG. 19 is an anterior view of the patient's distal femur illustrating the distal femoral cutting block after removal of the valgus block, stylus, and intramedullary rod and before the surgeon has made the distal femoral cut.

There are a series of five openings 39 and a series of five openings 40 provided on distal femoral cutting block 35. This allows the surgeon to select any particular one of the openings 39 and any particular one of the openings 40 or more than one of each of these openings 39, 40 for placement of bone pins therethrough. FIGS. 18 and 19 show bone pins 46, 47 in operative positions securing the distal femoral cutting block 35 to the anterior side of the patient's distal femur F.

Figure 25:
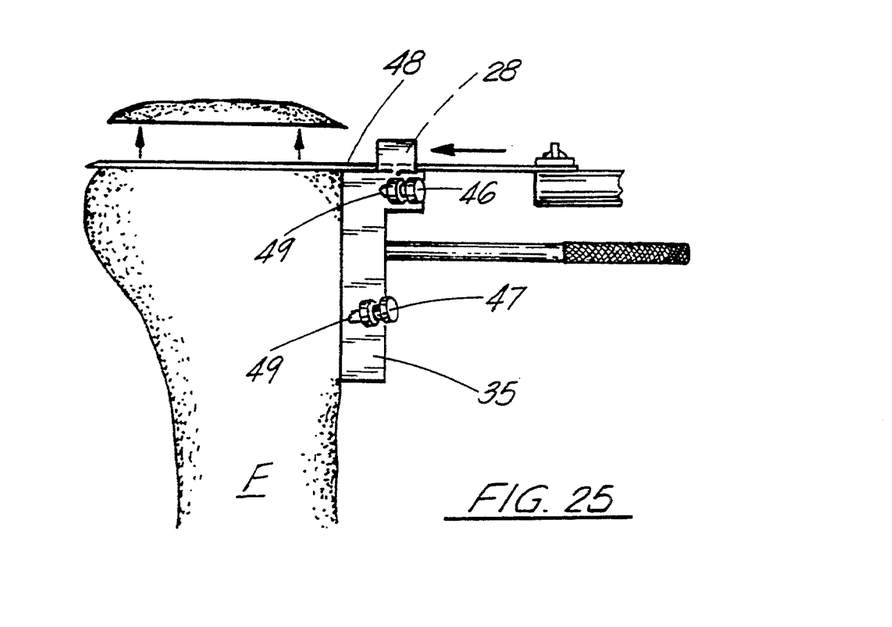
FIG. 25 is a partial side view of the preferred embodiment of the apparatus of the present invention illustrating the method step of making a distal cut on the patient's distal femur.

After the distal femoral cutting block 35 has been secured to the anterior aspect of the patient's distal femur F as shown in FIG. 18, the surgeon then removes three parts of the apparatus of the present invention, including the intramedullary rod 19, valgus block 10, and stylus 20. Locking screw 43 releases stylus 20 so that these parts 10, 19, and 20 can be removed. After removing these parts 10, 19, and 20, the distal femoral cutting block alone remains on the anterior side of the patient's distal femur F as shown in FIG. 19. The surgeon can now use a flat surgical cutting saw 48 (see FIG. 25) to cut bone tissue from the patient's distal femur.

After the distal femoral cut has been made (see FIG. 25), the surgeon removes cutting block 35 and places a gauge 50 on the patient's distal femur. The gauge is comprised of two members including anterior cutting block 51 and paddle body 52. The anterior cutting block 51 is provided with feeler gauge 53 has a tip or finger portion 54 that contacts the patient's femur at a position designated as 55 in FIG. 23 that is spaced away from the patient's distal femur.

Figure 24:
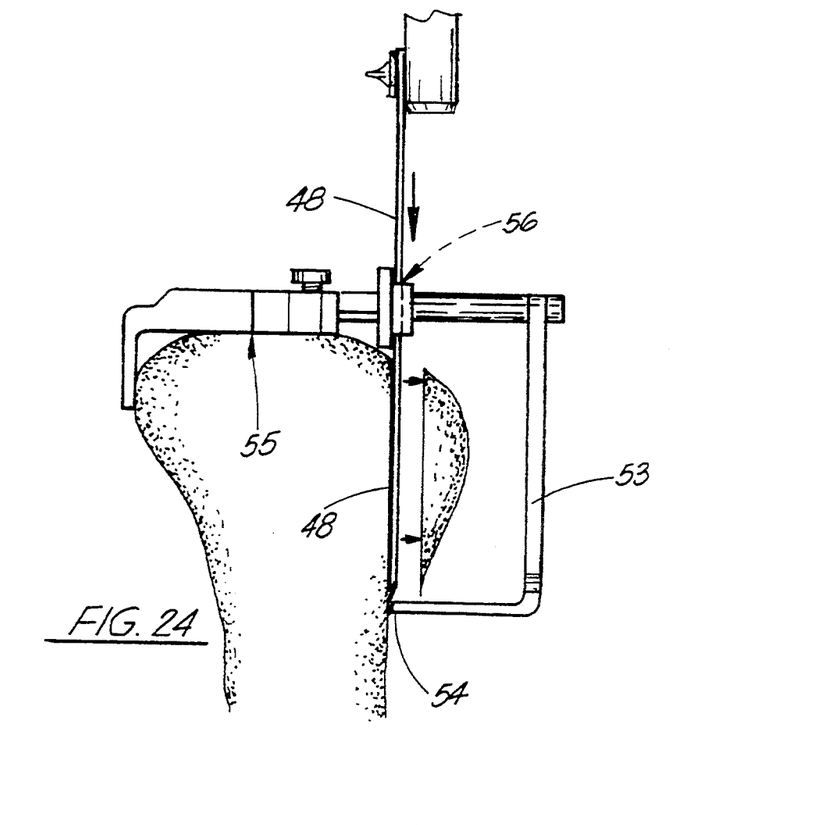
FIG. 24 is a partial side view of the referencing members illustrated during a cut of the anterior femoral cortex.

Anterior cutting block 51 also provides a transversely extending cutting guide slot 57 that guides a flat cutting saw 48 during a shaping of the patient's anterior cortex as shown on FIG. 24.

The paddle body 52 provides a pair of spaced apart paddles or feet 58, 59. Anterior cutting block 51 and paddle body 52 slidably engage one another in telescoping fashion. Paddle body 51 provides a pair of spaced apart parallel slots 60, 61 that are engaged by parallel rails 62, 63 of anterior cutting block 51.

Figures 22, 23:
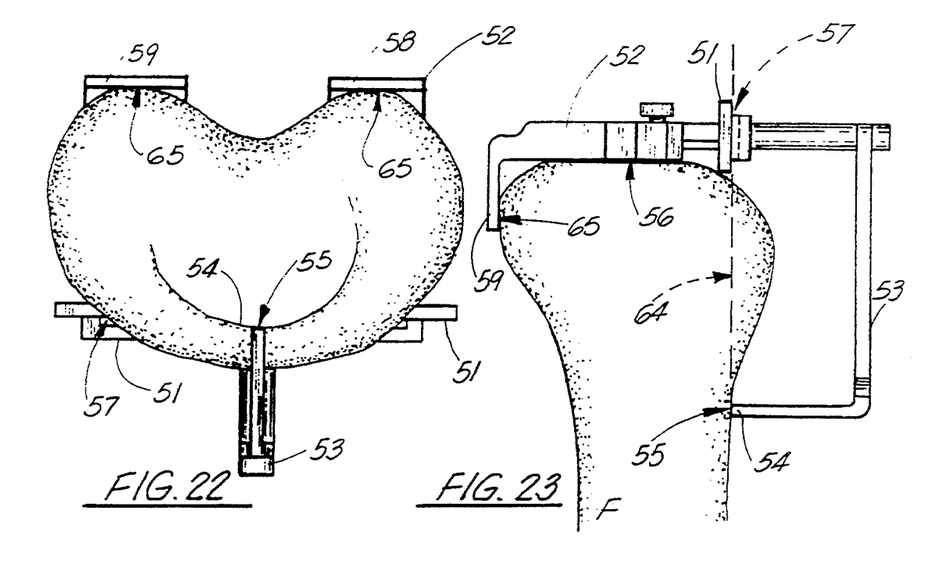
FIG. 22 is an end view of the gauge portions during a measurement of the patient's distal femur between anterior and posterior sides thereof.
FIG. 23 is a partial side view illustrating the gauge member of the preferred embodiment of the apparatus of the present invention.

As shown in FIGS. 23 and 24, the anterior cortical cut is made along line 64 that tracks between slot 57 and the tip 54 of feeler gauge 53. Before making the anterior cortical cut as designated by the line 64, the surgeon measures the patient's distal femur using the gauge 50. The measurement is defined as the distance between the anterior femoral cortex at position 55 (see FIG. 23) and the posterior condyles at 65 (see FIGS. 22–23).

The feeler gauge 51 and paddle body 52 slide or telescope with respect to one another during such a measuring of the anterior to posterior (from 55 to 65) surfaces of the patient's distal femur. When the surgeon has placed the gauge 50 upon the patient's distal femur F and in the position shown in FIGS. 20 and 23, an indicating means is provided for indicating the size of the prosthesis to be used by the surgeon. The indicating means includes a pair of rows of openings including an anterior row of openings designated by the numerals 66–69 and a posterior set of openings designated by the numerals 70–73, In FIG. 20, the letter "A" is placed beside the anterior referencing opening 66–69 and the letter "P" is placed beside the row of posterior referencing openings 70–73.

Figures 20, 21:
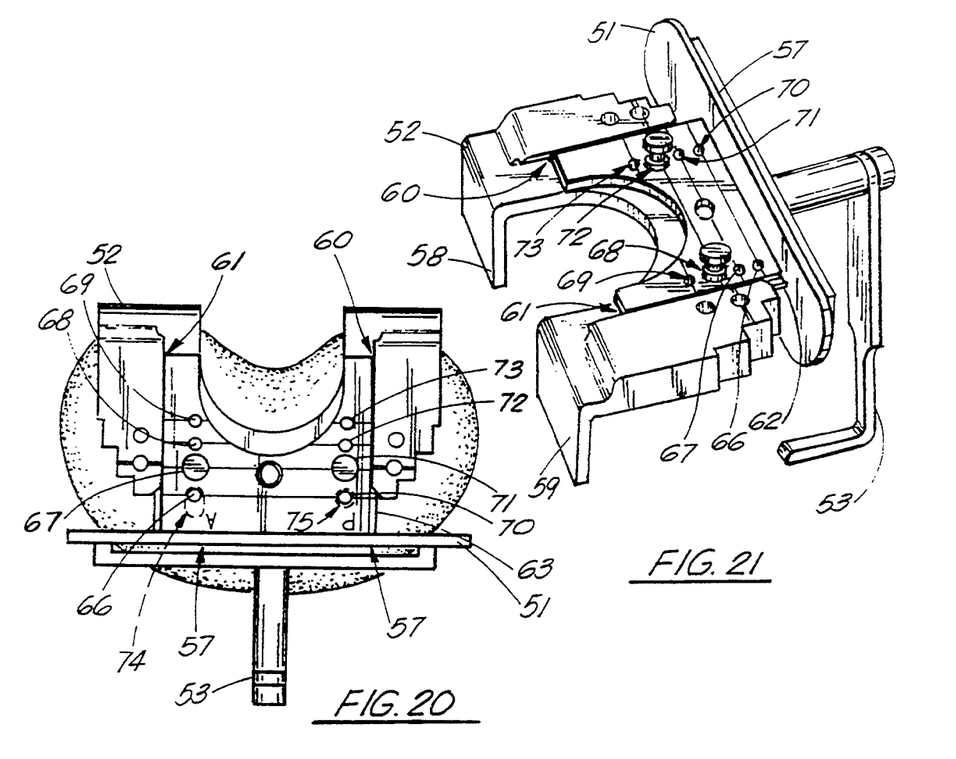
FIG. 20 is a distal end view of the patient's femur illustrating the paddle and feeler gauge portions thereof shown in operative position during a measurement of the patient's distal femur and prior to the anterior femoral cut.
FIG. 21 is a partial perspective view of the preferred embodiment of the apparatus of the present invention illustrating the gauge portions thereof as comprising referencing members for measuring the patient's distal femur between anterior and posterior sides thereof.

The paddle body 52 also provides anterior 74 and posterior 75 referencing openings. On the paddle body there is a single anterior referencing opening 74 and a single posterior referencing opening 75 that is an elongated opening in the form of an oval as shown in FIG. 20.

The anterior opening 75 on the paddle body 52 is oval shaped because when the surgeon uses an anterior referencing technique, the surgeon selects the next smallest available prosthesis size if the gauge 50 measures an anterior to posterior distal femoral dimension that is in between available prosthesis sizes. Therefore, the surgeon can place a bone pin through an opening 66–69 in the feeler gauge 53 that is smaller if the distance measured is in between sizes. This is because the elongated slot allows the surgeon the place the pin through the smallest available hole 66–69 even if the dimension is in between sizes. In FIG. 20, the smallest dimensional opening would be the opening designated as 66, and the largest opening would be the opening 69. The slot 75 is sized to be large enough to spin between any two adjacent openings such as 66, 67 68 or 69. In that regard, if the size falls in between two available sizes, the slot 65 allows the surgeon to always select the smaller of the two sizes. However, in posterior referencing, the surgeon uses the openings 70–73 and the rounded or circular opening 74 in paddle body 52. Because the opening 75 is rounded, the surgeon has to always go to a larger size prosthesis as defined by one of the adjacent openings 71–73 if the measurement falls in between sizes. Otherwise, the surgeon could not select a smaller size prosthesis because the paddles 58, 59 and feeler gauge 53 prevent a compression of the gauge members 51, 52 to a smaller dimension. However, the surgeon can simply enlarge the two gauge members 51, 52 until the openings 75 in the paddle body 52 aligns with the next largest opening 71, 72 or 73 in the anterior cutting block 51. Thus, when posterior referencing when the size prosthesis is indicated as in between available sizes, the surgeon is forced to always select the next largest size prosthesis.

In either case, the surgeon maintains contact of the paddles 58, 59 against the condyles 65. If a larger prosthesis is selected (posterior referencing), the surgeon expands the gauge 50 so that the tip 54 of feeler gauge 53 lifts away from cortical bone surface 55. The surgeon then makes the cut as shown in FIG. 24.

When using anterior referencing, the surgeon makes the cut on the anterior surface. More tissue will be removed from the posterior surface when anterior referencing because the surgeon selected the next smallest prosthesis size. The additional cut from the posterior distal femoral surface at condyle 65 will be made using a cutting block 76 that has a shoulder 77 which engages the patient's anterior cortex after the cut is made as shown in FIG. 23 and 24.

Figure 30:
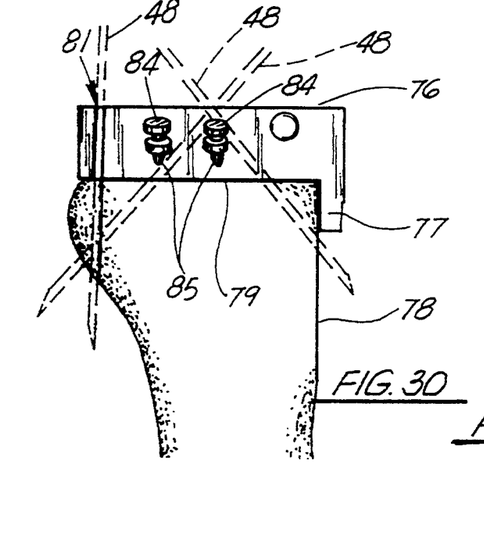
FIG. 30 is a side schematic view illustrating the cutting block portion of the preferred embodiment of the apparatus of the present invention and showing posterior and chamfer cuts.
Figure 31:
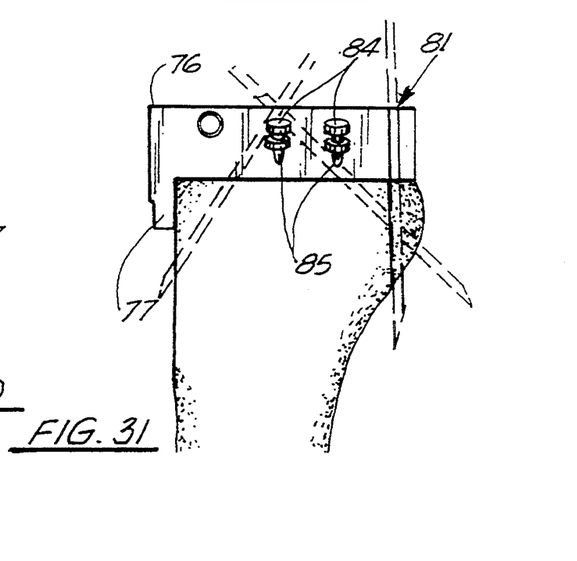
FIG. 31 is another side view illustrating the cutting block and chamfer and posterior cuts being made with the aid of the cutting block.

The cut on the anterior cortex is designated by the numeral 78 in FIG. 30. The distal femoral cut leaves a flat surface designated as 79 in FIG. 30. The bottom surface 80 of cutting block 76 is placed against the shaped distal femoral surface 79. The shoulder 77 is placed against the shaped distal femoral surface 78. The cutting block 76 is sized using the aforementioned anterior or posterior referencing technique. Cutting blocks 76 are available in various sizes depending upon the size prosthesis to be selected. Therefore, if the surgeon uses anterior referencing and selects the next smallest prosthesis size, there is a corresponding cutting block 76 for making the chamfer cuts and the posterior femoral cut.

The posterior femoral cut is made using slots 81 that are normal to bottom surface 80. Chamfer cuts are made using diagonal slots 81, 82. In FIG. 30, flat surgical cutting saw 48 is schematically shown in tracking the slots 81-83 for making the posterior and chamfer cuts. Bone pins 84 can be placed through diagonal openings 85 in cutting block 76 for holding the cutting block 76 in position.

Figure 26:
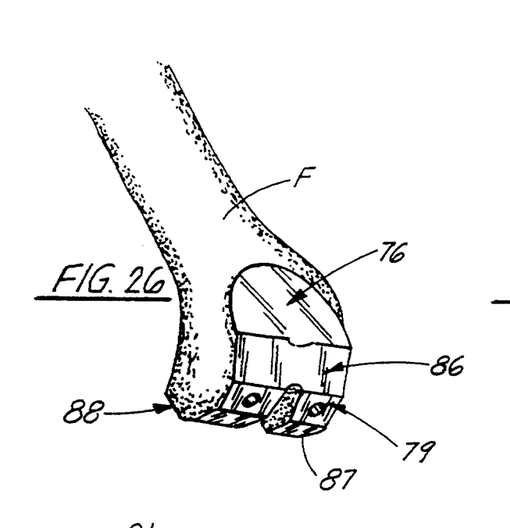
FIG. 26 is a perspective view of the patient's distal femur shown after all five cuts have been made using the method and apparatus of the present invention.
Figure 27:
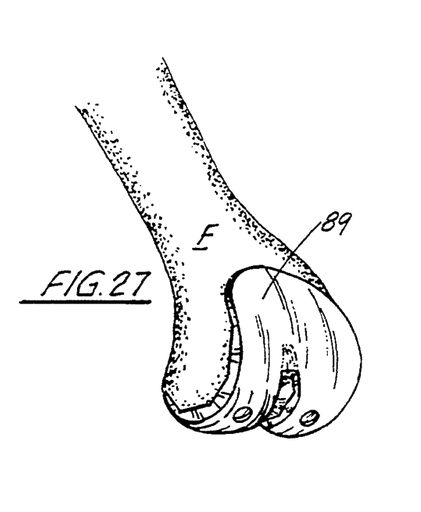
FIG. 27 is a partial perspective view illustrating a femoral prosthesis having been placed on the patient's distal femur after the five cuts have been made using the method and apparatus of the present invention.
Figure 28:
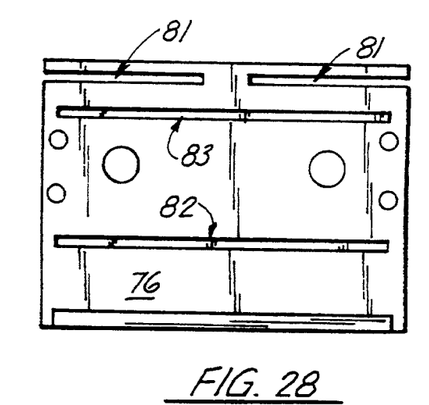
FIG. 28 is a top view of the cutting block portion of the preferred embodiment of the apparatus of the present invention.
Figure 29:
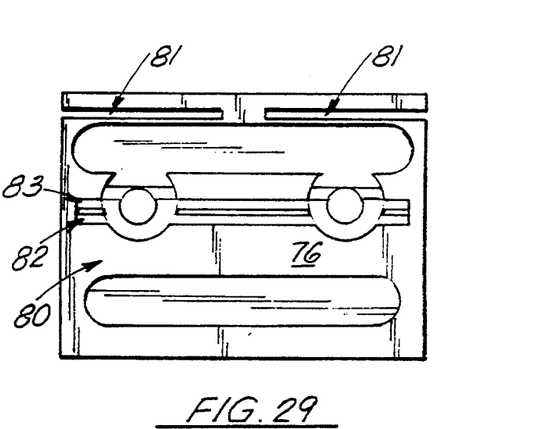
FIG. 29 is a bottom view of the cutting block portion of the preferred embodiment of the apparatus of the present invention.

In FIG. 26, the distal femur of the patient is shown after all cuts have been made including anterior cut 76, distal cut 79, chamfer cuts 86, 87 and posterior cut 88. In FIG. 27, a prosthesis 89 is shown in position on the patient's femur "F" after surgery is completed.

The following table lists the parts numbers and parts descriptions as used herein and in the drawings attached hereto.

| PARTS LIST | |
|---|---|
| Part Number | Description |
| 10 | valgus block |
| 11 | proximal flat surface |
| 12 | distal flat surface |
| 13 | flat surface |
| 14 | flat surface |
| 15 | side wall |
| 16 | side wall |
| 17 | angled bore |
| 18 | bore axis |
| 19 | intramedullary rod |
| 20 | stylus |
| 21 | base flange |
| 22 | flat edge |
| 23 | arm |
| 24 | post |
| 25 | post |
| 26 | opening |
| 27 | opening |
| 28 | locking nut |
| 29 | locking nut |
| 30 | beveled surface |
| 31 | beveled surface |
| 32 | upper surface |
| 33 | lower surface |
| 34 | dove tail section |
| 35 | distal femoral cutting block |
| 36 | dove tail slot |
| 37 | post |

-continued

| PARTS LIST | |
|---|---|
| Part Number | Description |
| 38 | slot |
| 39 | openings |
| 40 | openings |
| 41 | upper surface |
| 42 | lower surface |
| 43 | locking screw |
| 44 | threaded shank |
| 45 | threaded opening |
| 46 | bone pin |
| 47 | bone pin |
| 48 | flat surgical cutting saw |
| 49 | openings |
| 50 | gauge |
| 51 | anterior cutting block |
| 52 | paddle body |
| 53 | feeler gauge |
| 54 | tip |
| 55 | anterior femur |
| 56 | cut distal femoral surface |
| 57 | transverse slot |
| 58 | paddle |
| 59 | paddle |
| 60 | slot |
| 61 | slot |
| 62 | rail |
| 63 | rail |
| 64 | cut |
| 65 | condyle |
| 66 | opening |
| 67 | opening |
| 68 | opening |
| 69 | opening |
| 70 | opening |
| 71 | opening |
| 72 | opening |
| 73 | opening |
| 74 | paddle body opening |
| 75 | paddle body opening |
| 76 | cutting block |
| 77 | shoulder |
| 78 | shaped anterior femoral surface |
| 79 | shaped distal femoral surface |
| 80 | bottom surface |
| 81 | slot |
| 82 | slot |
| 83 | slot |
| 84 | bone pin |
| 85 | opening |
| 86 | chamfer cut |
| 87 | chamfer cut |
| 88 | posterior cut |
| 89 | femoral prosthesis |
| F | femur |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A distal femoral cutting instrument for preparing a patient's distal femur to receive a femoral prosthesis, the femur having anterior and posterior distal femoral surfaces, comprising:

a) an intramedullary rod for referencing the patient's intramedullary canal by aligning the rod with the patient's intramedullary canal;

b) a valgus block having a plurality of flat surfaces and including at least anterior and posterior parallel flat surfaces and a distal flat surface perpendicular to the anterior and posterior surfaces;

c) a bore in the valgus block that extends between two of the flat surfaces, forming an acute angle therewith, said bore being sized and shaped to register upon the intramedullary rod;

d) a distal femoral cutting block that removably attaches to the valgus block, the cutting block having a flat surface for guiding a blade or saw during cutting of the distal femur;

e) the cutting block including means thereon for affixing the distal femoral cutting block to the anterior cortical bone of the patients femur;

f) gauge means forming a sliding connection with the distal femoral cutting block for measuring the thickness of the patient's distal femur between the anterior and posterior surfaces thereof;

g) indexing means on the gauge means for indicating the thickness of the patient's distal femur, said indexing means including independent anterior and posterior referencing indicia, allowing the surgeon to measure the distal femur using either an the anterior or posterior referencing indicia.

2. The apparatus of claim 1 wherein the rod has an elongated linear axis.

3. The apparatus of claim 1 further comprising a stylus member that forms a removable connection between the valgus block and the distal femoral cutting block, the stylus comprising a flanged member with connection means thereon for removably attaching the member to the valgus block and to the cutting block.

4. The apparatus of claim 1 wherein the gauge means comprises a pair of movably connected gauge members that slide relative to one another.

5. The apparatus of claim 5 wherein the gauge means comprises a pair of gauge members that slidably engage one another.

6. The apparatus of claim 6 wherein each of the gauge members has a shoulder for engaging the anterior and posterior distal femoral surfaces during use.

7. The apparatus of claim 7 wherein the gauge members have means for affixing the position of the gauge members relative to one another and at a selected location on the distal femur.

8. A method of shaping the distal femur of a patient to receive a femoral prosthesis that is selected from a group of prostheses having anterior/posterior sizes that are differently sized in known dimensional increments and wherein the patient's distal femur has an anterior and posterior portions, comprising the steps of:

a) surgically placing one end of an elongated intramedullary rod in the patient's intramedullary canal at the distal femur;

b) referencing a cutting block with the intramedullary rod by affixing the block to the rod, the block having a cutting block body portion with a transverse reference surface for guiding a cutting instrument during cutting of the distal femur;

c) affixing the cutting block body to the anterior portion of the patient's distal femur;

d) removing at least the rod and a portion of the cutting block assembly to expose the distal femur so that a transverse cut can be made through the distal femur;

e) cutting the distal femur by guiding a cutting instrument with the transverse reference surface;

f) measuring the thickness of the distal femur between its anterior and posterior surface portions with an adjustable gauge that includes an anterior cortical cutting guide and indicia for indicating the size of a femoral prosthesis that will fit the patient's distal femur once shaping is completed;

g) selecting either an anterior or a posterior referencing surgical technique if the measured dimension falls in between available sizes;

h) selecting an anterior referencing technique by selecting the next smallest size prosthesis if the measured dimension is in between available prosthesis sizes;

i) selecting a posterior referencing technique by selecting the next largest size prosthesis if the measured dimension is in between available prosthesis sizes;

j) means for affixing the referencing means in a position that selects the next largest or the next smallest size prosthesis if the indicated size falls in between available prosthesis sizes;

k) affixing the gauge in a desired position using either anterior or posterior referencing to affix the cutting guide to the anterior cortical cutting guide gauge in either the next largest or next smallest prosthesis size if the gauge dimension falls in between sizes;

l) selecting a cutting block with cutting guide surfaces thereon for making distal femoral and transfer cuts that correspond to the prosthesis of the size selected.

9. The method of claim 8 further comprising the step of securing the cutting block to the rod at an opening in the cutting block.

10. The method of claim 8 further comprising the step of removing the valgus block and intramedullary rod from the patient's distal femur after the cutting block body has been secured to the distal femur.

11. The method of claim 8 further comprising the step of connecting the cutting block assembly to the valgus block with a stylus.

12. The method of claim 11 further comprising the step of removing the rod, stylus and valgus block from the distal femur.

13. A distal femoral cutting instrument for preparing a patient's distal femur to receive a femoral prosthesis, the femur having anterior and posterior distal femoral surfaces, comprising:

a) an intramedullary rod for referencing the patient's intramedullary canal by aligning the rod with the patient's intramedullary canal;

b) a valgus block having a plurality of flat surfaces and including at least anterior and posterior parallel flat surfaces and a distal flat surface perpendicular to the anterior and posterior surfaces;

c) a bore in the valgus block that extends between two of the flat surfaces, forming an acute angle therewith, said bore being sized and shaped to register upon the intramedullary rod;

d) a distal femoral cutting block that removably attaches to the valgus block, the cutting block having a flat surface for guiding a blade or saw during cutting of the distal femur;

e) the cutting block including means thereon for affixing the distal femoral cutting block to the anterior cortical bone of the patients femur;

f) gauge means forming a sliding connection with the distal femoral cutting block for measuring the thickness of the patient's distal femur between the anterior and posterior surfaces thereof;

g) indexing means on the gauge means for indicating the thickness of the patient's distal femur, said indexing means including independent anterior and posterior referencing indicia, allowing the surgeon to measure the distal femur using either an anterior or posterior referencing indicia.

14. A method of shaping the distal femur of a patient to receive a femoral prosthesis that is selected from a group of prostheses having anterior/posterior sizes that are differently sized in known dimensional increments and wherein the patient's distal femur has an anterior and posterior portions, comprising the steps of:

a) surgically placing one end of an elongated intramedullary rod in the patient's intramedullary canal at the distal femur;

b) referencing a cutting block with the intramedullary rod by affixing the block to the rod, the block having a cutting block body portion with a transverse reference surface for guiding a cutting instrument during cutting of the distal femur;

c) affixing the cutting block body to the anterior portion of the patient's distal femur;

d) removing at least the rod and a portion of the cutting block assembly to expose the distal femur so that a transverse cut can be made through the distal femur;

e) cutting the distal femur by guiding a cutting instrument with the transverse reference surface;

f) measuring the thickness of the distal femur between its anterior and posterior surface portions with an adjustable gauge that includes an anterior cortical cutting guide and indicia for indicating the size of a femoral prosthesis that will fit the patient's distal femur once shaping is completed;

g) selecting either an anterior or a posterior referencing surgical technique if the measured dimension falls in between available sizes;

h) selecting an anterior referencing technique by selecting the next smallest size prosthesis if the measured dimension is in between available prosthesis sizes;

i) selecting a posterior referencing technique by selecting the next largest size prosthesis if the measured dimension is in between available prosthesis sizes;

j) means for affixing the referencing means in a position that selects the next largest or the next smallest size prosthesis if the indicated size falls in between available prosthesis sizes;

k) affixing the gauge in a desired position using either anterior or posterior referencing to affix the cutting guide to the anterior cortical cutting guide gauge in either the next largest or next smallest prosthesis size if the gauge dimension falls in between sizes;

l) selecting a cutting block with cutting guide surfaces thereon for making distal femoral and transfer cuts that correspond to the prosthesis of the size selected.

* * * * *